(12) United States Patent
Carchidi et al.

(10) Patent No.: US 6,398,785 B2
(45) Date of Patent: *Jun. 4, 2002

(54) APPARATUS FOR RIGIDLY FIXING CRANIOMAXILLOFACIAL TISSUE GRAFTS AND BONE PLATES

(76) Inventors: Joseph Edward Carchidi, 132 Samuel Ave., West Bridgewater, MA (US) 02379; Alan R. Balfour, 5452 Quailridge Dr., Camarillo, CA (US) 93012

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/290,433

(22) Filed: Apr. 13, 1999

Related U.S. Application Data

(60) Provisional application No. 60/081,605, filed on Apr. 14, 1998.

(51) Int. Cl.[7] ............................................. A61B 17/56
(52) U.S. Cl. ......................................... 606/73; 411/387
(58) Field of Search ............................... 606/73, 70–72, 606/74, 75, 60–62; 411/387, 386, 384, 421, 416, 418, 378, 380, 411, 412, 414, 424, 402, 500; 85/41, 46, 47; 408/213, 224

(56) References Cited

U.S. PATENT DOCUMENTS

| | | | | |
|---|---|---|---|---|
| 411,000 A | * | 9/1889 | Anderson | 85/47 |
| 3,358,548 A | * | 12/1967 | Dyslin | 411/386 |
| 3,738,218 A | * | 6/1973 | Gutshall | 85/47 |
| 4,202,244 A | * | 5/1980 | Gutshall | 85/45 |
| 4,365,958 A | * | 12/1982 | Vlock | 433/225 |
| 4,509,767 A | * | 4/1985 | Brilando | 280/289 |
| 4,781,506 A | * | 11/1988 | Roberts et al. | 411/387 |
| 4,844,676 A | * | 7/1989 | Adamek | 411/386 |
| 5,214,987 A | * | 6/1993 | Fenton, Sr. | 411/404 |
| 5,244,327 A | * | 9/1993 | Whitesell | 411/386 |
| 5,674,037 A | * | 10/1997 | Lu | 411/410 |
| 5,690,489 A | | 11/1997 | Carchidi | |
| 5,882,161 A | * | 3/1999 | Birkelbach | 411/387 |
| 5,971,985 A | | 10/1999 | Carchidi et al. | |

* cited by examiner

Primary Examiner—Stephen P. Garbe
Assistant Examiner—Lien Ngo
(74) Attorney, Agent, or Firm—John A. Haug

(57) ABSTRACT

A self-drilling and tapping multi-drive bone screw (10) for rigid fixation of craniomaxillofacial tissue grafts and bone plates has a tip (12a) which incorporates a defined twist drill shaft with a sharp cutting point tip (12b) to easily pierce and drill a pilot hole and prepare for the insertion of self-tapping screw threads (12c). A cylindrical dome shaped head (14) for rigid fixation of craniomaxillofacial tissue grafts and geometrically sized bone plates is formed on the screw distal to the drilling and tapping features. A spline feature (14e) is incorporated into the cylindrically dome shaped head for easy pickup, assembly and insertion of the bone screw with a corresponding spline driver tool (20). The spline driver feature also allows the bone screw (10) to be driven with either a standard square or cross blade driver tool.

3 Claims, 2 Drawing Sheets

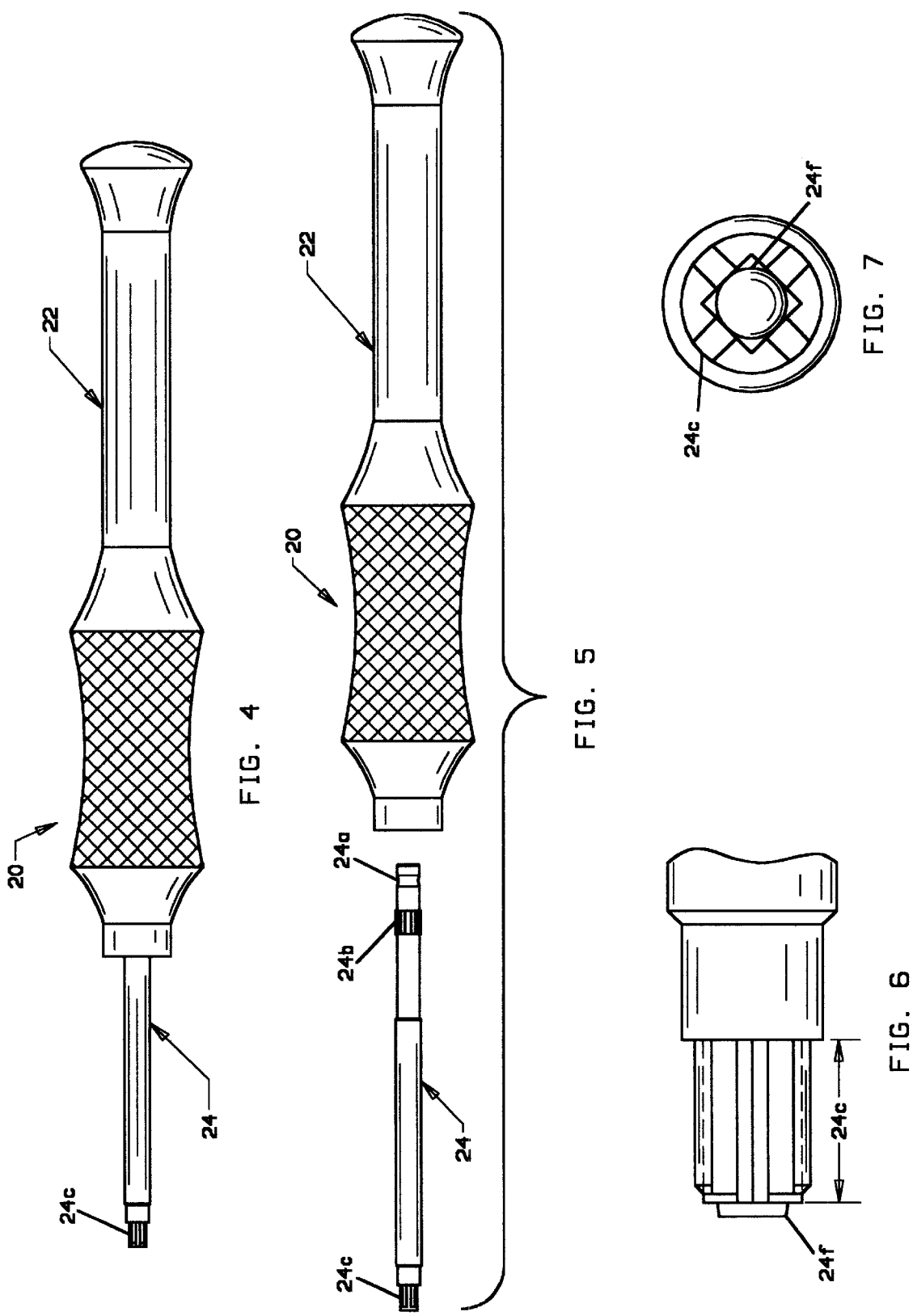

APPARATUS FOR RIGIDLY FIXING CRANIOMAXILLOFACIAL TISSUE GRAFTS AND BONE PLATES

RELATED APPLICATIONS

Benefit is claimed of U.S. Provisional Application No. 60/081,605, filed Apr. 14, 1998.

FIELD OF THE INVENTION

This invention relates generally to surgical apparatus and more particularly to bone screws for the retention of tissue grafts and bone plates.

BACKGROUND OF THE INVENTION

Presently, a variety of bone screws and surgical procedures are used for the retention of craniomaxillofacial tissue grafts and bone plates with a primary objective being to minimize the surgical steps and to maximize fixation. These procedures generally fall into one of two categories: a self-threading screw that incorporates a self-cutting flute to minimize the need to surgically prepare a pilot hole or a self-threading screw without a self-starting cutting flute which always requires a surgically prepared pilot hole.

For the latter type, the physician must perform multiple operations which involves first locating and drilling a pre-sized hole. Once the pilot hole is prepared, the physician must relocate the hole to insert the self-threading bone screw. Since most of the craniomaxillofacial procedures require small diameter bone screws, relocating the pilot hole prior to insertion of the bone screw can be difficult. However, the advantage to this procedure, if performed correctly, is that the pre-drilled pilot hole will act as a guide to insert the self-threading bone screw and minimize the risk of screw and/or bone fractures due to excessive applied seating torque.

To overcome the surgical requirements of drilling a pilot hole into a surgical site prior to inserting a bone screw, a variety of bone screw systems have incorporated a self-starting cutting flute into the apex of the screw. This self-starting cutting flute is designed to initially penetrate and cut into the bone site and then to lead the self-threading features of the screw into place. Although, conceptually, these screws eliminate the pitfalls of a pre-drilled hole and maximize the bone screw fixation, locating and inserting these screws become difficult. Since a pilot hole is not drilled, these screws are difficult to locate and start in the denser cortical bone and effectively become challenging to insert. In addition, these screws require substantially higher seating torque which lead to greater risk of screw or bone fracturing during insertion.

SUMMARY OF THE INVENTION

An object of the present invention is the provision of apparatus to overcome the above noted prior art limitations. Another object is the provision of apparatus for rigidly fixing craniomaxillofacial tissue grafts and bone plates in a single surgical procedure. These and other objects and features of the invention will be apparent from the following description taken with reference to the accompanying drawings.

Briefly stated, a bone screw made in accordance with the present invention incorporates a sharp piercing twist drill point tip in series with a self-tapping threaded body. A cylindrical dome shaped head is formed distal to the tip and body of the bone screw that drives the screw in or out of the surgical site using a unique spline driver tool. The invention solves the problems of locating and self-starting a self-tapping bone screw into place while minimizing the surgical steps and maximizing the fixation. This invention allows the physician to take advantage of a pre-drilled hole without compromising the surgical results common to the standard multiple step procedure. Finally, the component provides the physician with a cost effective, easy to use, functional equivalent to rigidly fix craniomaxillofacial tissue grafts and bone plates in a desired surgical site.

BRIEF DESCRIPTION OF THE DRAWINGS

FIG. 4 is a front elevational view of a delivery and drive tool for use with the FIG. 1 screw, FIG. 5 is a view, similar to FIG. 4 but exploded to show the separate components of the tool, FIG. 6 is an enlarged view of an end portion of the FIGS. 4 and 5 tool, and FIG. 7 is a left side elevational view of FIG. 6.

DETAILED DESCRIPTION OF THE PREFERRED EMBODIMENT

Figure 1:
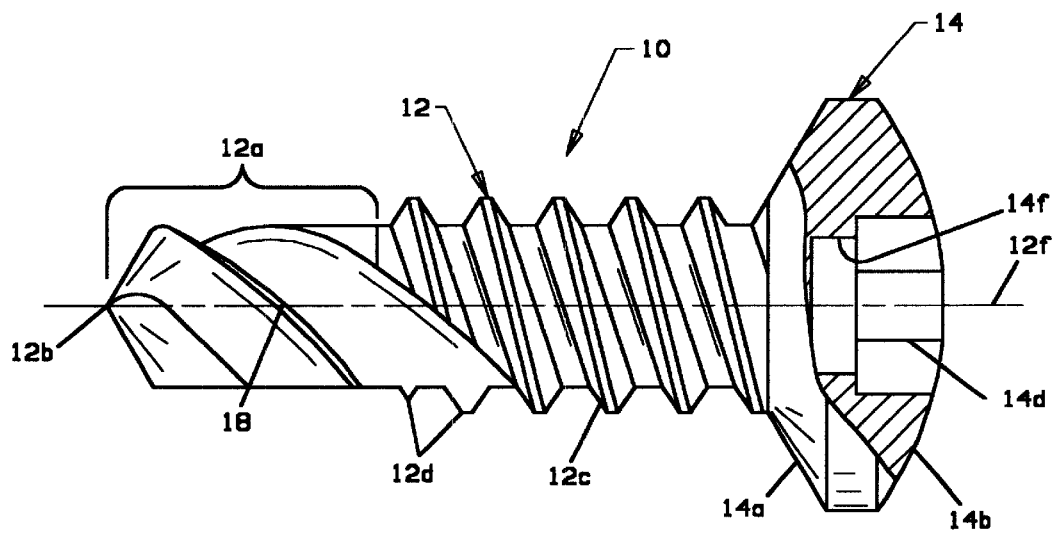
FIG. 1 is a front elevational view, partly in cross section, of a self-drilling and self-tapping bone screw made in accordance with the invention.
Figure 2:
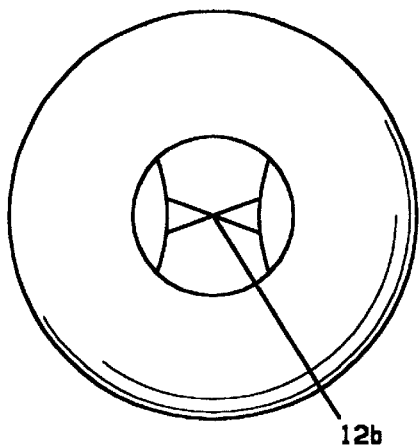
FIG. 2 is left side elevational view of the FIG. 1 screw.
Figure 3:
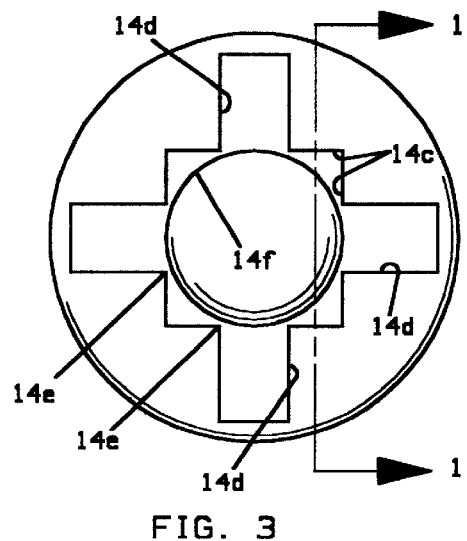
FIG. 3 is a right side elevational view of the FIG. 1 screw.

With reference to FIGS. 1–3, self-drilling and self-tapping bone screw 10 comprises a self-drilling and self-tapping bone screw cylindrical body 12 and cylindrical dome shaped driving head 14. The self-drilling and self-tapping bone screw cylindrical body 12 locates, drills and threads the screw body into the graft site with minimal effort while achieving maximum fixation. To achieve this, the self-drilling and self-tapping bone screw cylindrical body 12 incorporates a sharp twist drill point tip 12a with highly effective piercing and cutting tip 12b at one end of a longitudinal axis 12f to easily pierce and drill a pilot hole in preparation for the self-tapping thread 12c. The twist drill point tip 12a is selected to exactly match the diameter size of the shaft having the self-tapping thread 12c to further assist in the bone screw's insertion. The helical flutes 18 of the twist drill point tip 12a are extended along the drill shaft and into the first couple of threads of the larger diameter self-tapping screw threads 12c forming radially projecting flat surfaces to provide cutting flutes 12d for the bone screw's thread. These cutting flutes 12d aid in driving the self-tapping screw thread 12c down until the beveled seating neck 14a, to be discussed below, is completely seated.

The coronal end of the self-drilling and self-tapping bone screw 10 incorporates a cylindrical dome shaped head 14 for retention of the craniomaxillofacial tissue grafts and bone plates to the surgical site. On the inner side of the bone screw head 14 is a bevelled, or frusto-conical seating neck 14a that matches the standard mating bevel angle on bone screw plates (not shown). Opposite the beveled seating neck 14a is a smooth cylindrical dome shaped driving head 14b having an outer periphery which extends radially outwardly of the shaft portion of body 12. In the center of the driving head is a square recess 14c and a cross-slot recess 14d that, when combined, forms a unique female spline 14e along with a circular bore 14f formed inwardly of the square recess.

To deliver self-drilling and self-tapping screw 10 to the graft site, FIGS. 4–7 depict a press-fit, pick up and delivery spline driver tool 20. The body of the press-fit, pick-up and delivery spline driver tool 20 is made up of a detachable insert driver 24 and an oversized handle 22. The detachable insert driver 24 is connected and driven by the oversized handle 22 utilizing a coronal insert annular groove 24a and central milled polygonal feature 24b, such as hexagonal, at one end. Bone screw spline driver head 24c is formed at the opposite end from the connecting and driving features 24a and 24b of detachable insert driver 24. This male spline driver head is made up of a combined cylindrical shaft tip 24f having a frictional locking taper that frictionally locks into bore 14c having an appropriately sized diameter in bone screw 10. The friction lock allows bone screw 10 to be easily picked up and delivered by the physician to the surgical site to prevent any risk of contamination.

Placing the twist drill tip in series with the self-tapping threads allows the physician to insert the bone screw in a single surgical procedure. As the bone screw is driven into the surgical site, bone chips will fill the space left by the helical cutting flutes that extend along the drill shaft and into the first couple of threads of the self-tapping screw. Once inserted in the bore formed by the drill shaft body, the self-tapping threads of the bone screw are engaged to rigidly fix and drive the screw into place.

It should be understood that this invention includes all modifications and equivalents of the described embodiment falling within the scope of the appended claims.

What is claimed:

1. Apparatus for retention of tissue grafts and bone plates to a bone site comprising an elongated bone screw body member having a generally cylindrical shaft having a longitudinal axis and a selected diameter and first and second opposite end portions, a sharply pointed, piercing and cutting tip formed at the first end portion aligned with the longitudinal axis, helical drill flutes formed on the shaft along a first axial length of the shaft having an outer diameter generally equal to the selected diameter, the helical drill flutes being separated from one another by generally line contact along the first axial length, self-tapping bone screw threads formed on the shaft along a second axial length of the shaft, the bone screw threads having an inner diameter generally equal to the selected diameter and being contiguous with the first axial length, the self-tapping bone screw threads having a second outer diameter greater than the selected diameter, the helical drill flutes aligned with and forming a continuation of the self-tapping bone screw threads along a first portion of the second axial length forming cutting flutes and a driving head formed at the second end portion of the shaft, the driving head extending radially outwardly beyond the shaft forming an outer most periphery and being formed with a frusto-conical surface extending from the outer most periphery to the shaft, the diameter of the frusto-conical surface increasing in a direction going from the first end portion to the second end portion, and a female driving spline formed at the second end portion of the member aligned with the longitudinal axis of the body member, the female driving spline comprises a polygonal central recess and a radially extending slot communicating with the central recess, and a circular bore extending along the longitudinal axis, the circular bore being in communication with, and extending beyond, the central recess.

2. A driving tool for use with a threaded member having a longitudinal axis and having a female driving spline formed at an end thereof having a central recess having polygonal sides of a selected number, the sides each being generally flat and lying in a plane extending parallel to the longitudinal axis, a radially extending slot communicating with the central recess and intersecting at least one of the sides and a cylindrical bore in communication with, and extending beyond, the central recess, comprising an elongated body member having a longitudinal axis, the member having a polygonally shaped end portion having the selected number of sides, the sides each being generally flat and lying in a plane extending parallel to the longitudinal axis of the elongated member and having a size chosen to closely fit within the polygonal sides of the central recess, a blade portion extending outwardly from the polygonally shaped end portion having a configuration chosen to be closely received in the at least one radially extending slot and a generally cylindrical male holding portion extending along the longitudinal axis of the elongated member beyond the polygonal shaped portion, the generally cylindrical male holding portion formed with a friction locking taper to closely fit within the cylindrical bore of the spline.

3. Apparatus for retention of tissue grafts and bone plates to a bone site comprising an elongated body member having a generally cylindrical shaft first and second opposite end portions, a sharply pointed, piercing and cutting tip formed at the first end portion aligned with the longitudinal axis, helical drill fluted formed on the shaft along a first axial length of the shaft having an outer diameter generally equal to the selected diameter, self-tapping bone screw threads formed on the shaft along a second axial length of the shaft, the bone screw threads having an inner diameter generally equal to the selected diameter, the helical drill flutes aligned with and forming a continuation of the self-tapping bone screw threads along a first portion of the second axial length forming cutting flutes and a driving head formed at the second end portion of the shaft, the driving head extending radially outwardly beyond the shaft forming an outer periphery and being formed with a frusto-conical surface extending from the outer periphery to the shaft and a female driving spline formed at the second end portion of the member aligned with the longitudinal axis of the body member, the female driving spline having side surfaces forming a polygonally shaped recess, the side surfaces each being generally flat and lying in a plane which is parallel to the longitudinal axis of the body member, at least one radially extending blade shaped slot communicating with the recess, a cylindrical bore extending along the longitudinal axis of the body member in communication with and extending beyond the polygonally shaped recess, an elongated tool member having a longitudinal axis and having a polygonally shaped portion having the selected number of sides, the sides each being generally flat and lying in a plane extending parallel to the longitudinal axis of the tool member and having a size chosen to closely fit within the polygonally shaped recess, a blade portion extending from the polygonally shaped portion having a configuration chosen to be closely received in the at least one radially extending slot and a generally cylindrical male holding portion extending along the longitudinal axis of the elongated member beyond the polygonally shaped portion, the generally cylindrical male holding portion formed with a friction locking taper configured to closely fit within the cylindrical bore of the spline.

* * * * *